(12) United States Patent
Modi

(10) Patent No.: US 11,786,475 B2
(45) Date of Patent: Oct. 17, 2023

(54) FILM-BASED DOSAGE FORM

(71) Applicant: Pankaj Modi, Ancaster (CA)

(72) Inventor: Pankaj Modi, Ancaster (CA)

(73) Assignee: Soluble Technologies Inc., White Plains, NY (US)

( * ) Notice: Subject to any disclaimer, the term of this patent is extended or adjusted under 35 U.S.C. 154(b) by 308 days.

(21) Appl. No.: 16/935,853

(22) Filed: Jul. 22, 2020

(65) Prior Publication Data
US 2022/0023224 A1    Jan. 27, 2022

(51) Int. Cl.
*A61K 9/48* (2006.01)
*A61K 31/05* (2006.01)
*A61K 31/352* (2006.01)

(52) U.S. Cl.
CPC .......... *A61K 9/4825* (2013.01); *A61K 9/4858* (2013.01); *A61K 9/4866* (2013.01); *A61K 31/05* (2013.01); *A61K 31/352* (2013.01)

(58) Field of Classification Search
CPC ........................... A61K 9/4825; A61K 9/4866
See application file for complete search history.

(56) References Cited

U.S. PATENT DOCUMENTS

| | | | |
|---|---|---|---|
| 5,439,686 | A | 8/1995 | Desai et al. |
| 5,989,583 | A | 11/1999 | Amselem |
| 6,350,458 | B1 | 2/2002 | Modi |
| 6,849,263 | B2 | 2/2005 | Modi |
| 8,623,401 | B2 | 1/2014 | Modi |
| 10,555,901 | B2 | 2/2020 | Zhao et al. |
| 2009/0117180 | A1 | 5/2009 | Orenz et al. |
| 2012/0231083 | A1 | 9/2012 | Carley |
| 2015/0366815 | A1* | 12/2015 | Teles ............... A61K 9/4825 514/769 |
| 2017/0252300 | A1* | 9/2017 | Modi ............... A61K 31/352 |

FOREIGN PATENT DOCUMENTS

| | | |
|---|---|---|
| CA | 2194890 | 1/1996 |
| CA | 2222120 | 12/1996 |
| CA | 2268187 | 4/1998 |
| CA | 2229286 | 8/1999 |
| CA | 2354148 | 6/2000 |
| CA | 2382535 | 3/2001 |
| CA | 2391923 | 5/2001 |
| CA | 2428535 | 6/2002 |
| CA | 2493786 | 2/2004 |
| CA | 2518918 | 11/2004 |
| CA | 2589993 | 6/2006 |
| CA | 2624110 | 11/2010 |
| CA | 2922959 | 6/2016 |
| CA | 3020798 | 10/2017 |
| CA | 3053158 | 8/2018 |
| CA | 3059056 | 12/2018 |
| CA | 3061086 | 5/2020 |
| EP | 1897543 | 3/2008 |
| WO | 2001072278 | 4/2001 |
| WO | 200172278 | 10/2001 |
| WO | 2004043445 | 5/2004 |
| WO | 2007062494 | 6/2007 |
| WO | 2009015456 | 2/2009 |
| WO | 2010002418 | 1/2010 |
| WO | 2013009928 | 1/2013 |
| WO | 2015068052 | 5/2015 |

OTHER PUBLICATIONS

Vieira, M.G.A. et al. "Natural-based plasticizers and biopolymer films: A review" European Polymer Journal 47 (2011) 254-263 (Year: 2011).*
International Search Report PCT/CA2020/050737—dated Aug. 18, 2020.
Written Opinion PCT/CA2020/050737—dated Aug. 18, 2020.
Kelapu, S. et al.—Insoluble Drug Delivery Strategies: Review of Recent Advances and Business Prospects, Acta Pharm Sin B. Sep. 2015, vol. 5, No. 5, pp. 442-453 ISSN 2211-3835.
Singh et al.—Oral Formulation Strategies to Improve Solubility of Poorly Water Soluble Drugs, Expert Opin Drug Deliv, Oct. 2011, vol. 8, No. 10, pp. 1361-1378 ISSN 1744-5247.
European Search Report—EP 17759030.4.
Pathare et al.—"Polymers used for Fast Disintegrating Oral Films: A Review", Int J. Pharm Sci. Rev Res., 21(1), Jul.-Aug. 2013; No. 29, 169-178.
Shrestha et al.—"Nanoparticle processing: Understanding and controlling aggregation", Advances in Coolid and Interface Science, 279 (2020) 102162.
Smith et al.—"Dispursing nanoparticles in a polymer matrix: are long, dense polymer tethers really necessary?", Langmuir, Oct. 6, 2009:25 (19); 11239-43.
Liu et al.—"Nanoparticle Dispersion and Aggregation in Polymer Nanocomposites: Insights from Molecular Dynamics Simulation", Langmuir, 2011, 27, 7926-7933.
Lv et al.—"Mucoadhesive bucal films containing phospholipid-bile salts-mixed micelles as an effecitve carrier for Cucurbitacin B delivery", Drug Deliv, 2015; 22(3):351-358.

* cited by examiner

*Primary Examiner* — Andrew S Rosenthal
(74) *Attorney, Agent, or Firm* — Gowling WLG (Canada) LLP

(57) ABSTRACT

A film-based dosage form is provided. The dosage form includes a film base comprising a film-forming agent, a plasticizer and a solvent; and a matrix incorporated within the film base which comprises a target molecule that exhibits low aqueous solubility which is encapsulated and solubilized in a micellar formulation comprising a detergent in an aqueous solvent. The dosage form is particularly useful for administration of cannabinoids.

20 Claims, 2 Drawing Sheets

Cut Films (2.5inch x 2.1inch)

FILM-BASED DOSAGE FORM

FIELD OF THE INVENTION

The present invention generally relates to oral dosage forms, and in particular, relates to dissolvable film-based dosage forms such as capsules, and their use as a delivery vehicle for molecules with low solubility.

BACKGROUND OF THE INVENTION

*Cannabis* compounds have a long history of use in humans as an anticonvulsant, sedative, hypnotic, anti-depressant, analgesic, anti-inflammatory, anti-emetic, anti-spasmodic, and appetite-stimulator. *Cannabis* contains a broad spectrum of chemical compounds including: phytocannabinoids, terpenoids (essential oils), flavonoids, enzymes, and biosynthetic cannabinoids and derivatives. While delta-9-tetrahydrocannabinol (delta-9-THC) is believed to be the principle psychoactive component of *Cannabis* or hemp, other phytocannabinoids (such as cannabidiol, cannabinol, and cannabichromene) are thought to possess numerous medicinal properties without the psychoactive effects of delta-9-THC.

Due to the many desirable properties of phytocannabinoids, it would be advantageous to provide phytocannabinoid formulations with enhanced bioavailability for human consumption in various convenient dosage forms. Furthermore, there presently exists the need to provide more effective and safer *cannabis* delivery systems for various medical uses, and methods that provide unique active compounds that are useful to treat pain and various medical conditions.

Scientists have explored various administration routes for cannabinoids, its derivatives and large molecules in general. Other than injection, administration routes including oral, intranasal, rectal and vaginal have been considered for the delivery of large molecules. Oral and intranasal delivery are of interest because oral and nasal membranes offer advantages over other routes of administration. For example, drugs administered through these membranes have a rapid onset of action, provide therapeutic plasma levels, avoid first pass effect of hepatic metabolism, and avoid exposure of the drug to the hostile gastrointestinal environment. Additional advantages include ready access to the membrane sites providing for convenient application, localization and removal of the drug. Further, these membranes provide the potential for prolonged delivery of large molecules.

In addition, to the fact that the oral cavity is easily accessible and convenient, oral membranes such as the sublingual mucosa and the buccal mucosa, are relatively permeable, thereby providing ready absorption of orally administered drugs, and thus, improved bioavailability. The ability of molecules to permeate through the oral mucosa appears to be related to molecular size, lipid solubility and charge. Small molecules, less than 1000 daltons, appear to cross the mucosa readily. As molecular size increases, molecular permeability decreases. However, lipid soluble compounds are more permeable than non-lipid soluble molecules. Further, neutral or non-ionized molecules exhibit greater absorption than charged molecules.

While some penetration enhancing products have been determined to facilitate mucosal administration of large molecule drugs, e.g. greater than 1 kD, very few penetration enhancers have been approved for market use due to lack of a satisfactory safety profile, lowering of mucosal barrier function, impairment of the mucocilliary clearance protective mechanism, and due to the incidence of irritant properties. In addition, penetration enhancers are extremely bitter and unpleasant in taste. Several approaches have been utilized to improve the taste of enhancers, but none has been approved for human consumption to date.

Thus, it would be desirable to develop a formulation effective for the delivery of poorly soluble therapeutic or nutritive compounds, for example, macromolecules such as carbohydrates, lipids, proteins, and nucleic acids, as well as large compounds with low solubility such cannabinoids.

SUMMARY OF THE INVENTION

A novel orally administrable film-based dosage form is herein provided designed to effectively deliver large molecules or molecules having low solubility.

Thus, in one aspect, a film-based dosage form is provided comprising:
i) a film base comprising a film-forming agent, a plasticizer and a solvent; and
ii) a matrix incorporated within the film base comprising a target molecule that exhibits low aqueous solubility which is encapsulated in a micellar formulation comprising a detergent in an aqueous solvent.

In another aspect, a soft gel capsule is provided comprising:
i) an outer shell comprising a film-forming agent, a plasticizer and a solvent; and
ii) an inner matrix encapsulated within the outer shell, said matrix comprising a target molecule that exhibits low aqueous solubility which is encapsulated in a micellar formulation comprising a detergent in an aqueous solvent.

In a further aspect, a film-based dosage form is provided comprising: i) a film base in the form of a capsule shell comprising a film-forming agent, a plasticizer and a solvent; and ii) a matrix contained within the capsule shell comprising a target molecule that exhibits low aqueous solubility, a detergent, a lipase, a plasticizing agent, an emulsifying agent and an aqueous solvent, wherein the target molecule is solubilized in the matrix.

These and other aspects of the invention are described herein by reference to the following figures.

DETAILED DESCRIPTION OF THE INVENTION

Figure 1:
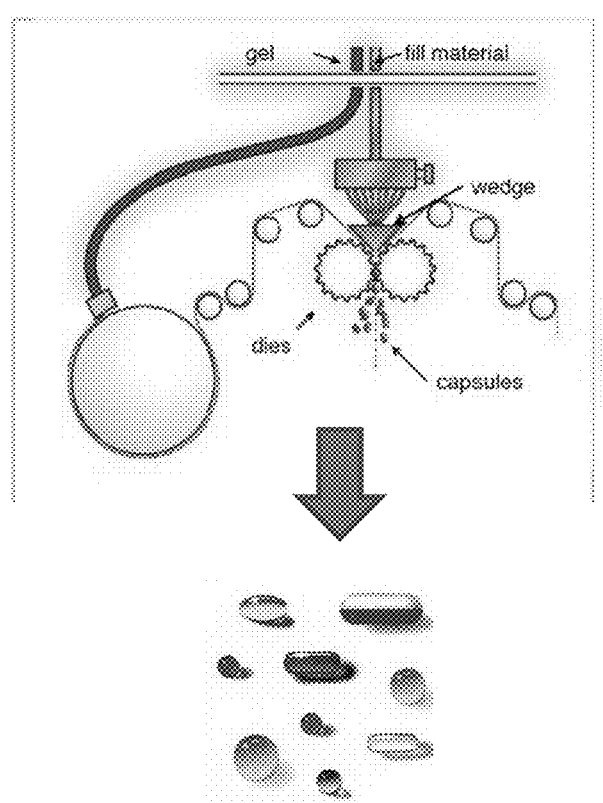
FIG. 1 generally illustrates a rotary die encapsulation process.

A film-based dosage form is provided comprising: a film base comprising film-forming agent, a plasticizer and a solvent; and a matrix within the film base comprising a target molecule that exhibits low aqueous solubility which is encapsulated in a micellar formulation comprising a detergent in an aqueous solvent.

The term "low solubility" as it used herein with respect to the target molecule refers to compounds in which greater than 30 mass parts of solvent is required to dissolve 1 mass part of compound or solute. The term "low solubility" encompasses degrees of solubility, for example, sparingly soluble in which 30-100 mass parts of solvent is required to dissolve 1 mass part of compound, slightly soluble in which 100-1000 mass parts of solvent is required to dissolve 1 mass part of compound, very slightly soluble in which 1000-10,000 mass parts of solvent is required to dissolve 1 mass part of compound, and insoluble in which greater than 10,000 mass parts of solvent is required to dissolve 1 mass part of compound. Low aqueous solubility refers to low solubility in water, or other aqueous-based solvents.

Film Base

The film base of the present dosage form comprises at least one film-forming agent, a plasticizer and a solvent. The film base may also optionally comprise excipients, sweeteners, flavourants, colourants, and the like.

Film Forming Agent

The film base comprises at least one physiologically acceptable primary film forming agent. Suitable film forming agents are hydrophilic compounds that form a pliable, cohesive and continuous film that exhibits rapid dissolution in aqueous solution. Examples of suitable film forming agents, include but are not limited to, gelatin, pullulan, alginic acid or alginate, collagen, methyl cellulose, ethyl cellulose, sodium carboxymethyl cellulose, hydroxypropylmethyl cellulose, hydroxyethyl cellulose, hydroxypropyl cellulose, carboxymethyl cellulose, polyvinyl pyrrolidone, methacrylic acid polymers, methacrylic acid copolymers, acrylic acid polymers, acrylic acid copolymers, polyacrylic acid, acrylate or methylmethacrylate copolymers, polyacrylamides, polyalkylene oxides, carrageanan, polyvinyl alcohol, sodium alginate, polyethylene glycol, glycolide, polylactide, carboxyvinyl polymer, amylose, high amylose starch, hydroxypropylated high amylose starch, pea starch, dextrin, pectin, chitin, chitosan, levan, elsinan and mixtures thereof.

Secondary film forming agents may be combined with the primary film forming agent to optimize the characteristics of the film such as tensile strength, stability and flexibility. Examples of suitable secondary film forming agents include xanthan gum, tragacanth gum, guar gum, locust bean gum, acacia gum, arabic gum, zein, gluten, soy protein isolate, whey protein isolate, casein and mixtures thereof.

Generally, the film comprises at least about 10% to about 80% by wt of film forming agent, including primary and secondary film forming agent. Preferably, the film comprises about 20% to about 60% of one or more film-forming agents. The term "about" is used herein to refer to an amount of a component outside of the listed amounts which would be understood by one of skill in the art to have little or no effect on the functionality of the product. The value attributed to the term "about" will vary from instance to instance, but may be a difference of 25%, more or less, from the listed amount or less, e.g. 20%, 15%, 10% or less.

In one embodiment, the film-forming agent comprises one or more of gelatin, collagen, acrylates, methacrylates or copolymers thereof, pectin and alginate, or combinations thereof.

In one embodiment, gelatin is used as the film forming agent. The gelatin may be a Type A or Type B gelatin. Type A gelatin is derived from the acid hydrolysis of collagen (e.g., acid bone gelatin or pig skin gelatin), while Type B gelatin (e.g., lime bone gelatin) is derived from the alkaline hydrolysis of collagen. Traditionally, bovine bones and skins are used as raw materials for manufacturing Type A and Type B gelatin, while porcine skins are used extensively for manufacturing Type A gelatin. In addition, at neutral pH values, Type A gelatins (acid processed gelatins) are typically net cationic (e.g., isoelectric point of about 7-9) and Type B gelatins (alkali processed gelatins) are typically net anionic (e.g., isoelectric point of about 4.5-5.3). Type A gelatin typically has higher plasticity and elasticity than Type B gelatin, while Type B gelatin typically has higher gel strength than Type A gelatin and other film forming polymers. Suitable gelatins have a Bloom strength in the range of about 50 Bloom to about 400 Bloom, and preferably in the range of 100 to 300, e.g. 200-250. Bloom strength is the weight (in grams) needed by a 0.5-inch diameter probe to deflect the surface of a gel 4 mm without breaking it. Examples of suitable gelatins for use in the present capsule shell include acid bone gelatin, pig skin gelatin, chicken skin gelatin, fish gelatin, acid hide gelatin, gelatin hydrolysate, lime bone gelatin, and combinations thereof.

In another embodiment, the film comprises a combination of a film-forming agent and gelatin hydrolysate. In this regard, gelatin is further defined as hydrolyzed collagen substantially comprising peptides of greater than 5 kDa in size, e.g. 5-25 kDa, while gelatin hydrolysate is defined as substantially comprising peptides of 5 kDa or less, e.g. 1-3 kDa in size. Gelatin hydrolysate is a non-gelling liquid. The term "substantially" is used to refer to a peptide content in the particular size range of at least about 90% in the gelatin or gelatin hydrolysate product, and preferably, a peptide content of at least 95% in the gelatin or gelatin hydrolysate. The film may comprise the film forming agent, e.g. gelatin, in an amount in the range of about 10-30% by weight and gelatin hydrolysate in an amount in the range of about 20-50% by weight of the film.

In another embodiment, the film is prepared by combining gelatin with one or more hydrolyzing agents to form a mixture of gelatin and gelatin hydrolysate in situ. In this regard, gelatin in an amount of about 10-80% by weight, preferably 20-60% by wt, e.g. 25%, 30%, 35%, 40%, 45% or 50% by wt, is combined with a hydrolyzing agent sufficient to further hydrolyze the gelatin into gelatin hydrolysate in an amount in the range of about 20-50% by wt of the film. The hydrolyzing agent may be a proteolytic enzyme such as an endopeptidase, e.g. trypsin, chymotrypsin, papain, pepsin and elastase, or an exopeptidase, e.g. aminopeptidase and carboxypeptidase A. As one of skill in the art will appreciate, suitable proteases include serine, cysteine, aspartic, threonine, glutamic acid, metalloproteases and mixtures thereof. The protease may be prokaryotic or eukaryotic. The hydrolyzing agent may also be a reagent-based, e.g. 1,1-diphenyl-2-picrylhydrazyl (DPPH), reduced L-glutathione (GSH), hydroxyproline, and the ACE synthetic substrate hippuryl-L-histidyl-L-leucine (HHL). The amount of the one or more hydrolyzing agents for the in situ formation of gelatin hydrolysate will vary with the agent used, e.g. enzyme or reagent-based agent, as will be appreciated by one of skill in the art.

Plasticizer

The film also comprises a plasticizer. As used herein, a plasticizer is a substance, often a polyol, that provides flexibility and softens the capsule. Examples include, but are not limited to, glycerol (glycerin), sorbitol, maltitol, mannitol, xylitol, triacetin, monoacetin, diacetin or combinations thereof. In one embodiment, the plasticizer comprises glycerol, maltitol, xylitol, or combinations thereof. The film generally comprises about 30% to about 70% of one or more plasticizers. The ratio of film forming agent to plasticizer in film is about 1:1 to about 1:2.

Polymer Modifiers

The film may optionally comprise one or more polymer modifiers. Polymer modifiers are chemicals that are added to a polymer matrix to improve the processability of the polymer matrix, enhance the shelf life of the polymer product, or otherwise modify the polymer matrix in a desired way. One of skill in the art is familiar with chemicals that may be used as polymer modifiers to modify a given polymer matrix. In one embodiment, the polymer modifier comprises an organic acid such as citric acid, acetic acid, lactic acid, malic acid, tartaric acid, glutamic acid, aspartic acid, malic acid, succinic acid, fumaric acid, or combinations thereof. In a preferred embodiment, the polymer modifier comprises citric acid. The one or more polymer modifiers may comprise about 0.01% to about 2% by weight of the film, and preferably, about 0.5% to about 2% by weight of the film.

Solvent

The film comprises one or more solvents. In one embodiment, the solvent comprises water. The solvent is present in the film in an amount of about 10% to about 40% by weight of the film.

Sweetener

The film may also comprise one or more sweeteners, such as bulk sweeteners, sugar sweeteners, sugar substitute sweeteners, artificial sweeteners, high-intensity sweeteners, or any combination thereof. Suitable bulk sweeteners include both sugar and non-sugar sweetening components. Useful sugar sweeteners include, but are not limited to, sucrose, dextrose, maltose, dextrins, trehalose, D-tagatose, dried invert sugar, fructose, levulose, galactose, corn syrup solids, and the like. Sugar substitutes include, but are not limited to, sorbitol, mannitol, xylitol, hydrogenated starch hydrolysates, maltitol, isomalt, erythritol, lactitol and the like. Artificial sweeteners include sucralose, aspartame, acesulfame potassium, acesulfame salts, steviol glycosides (e.g., Stevia®, Truvia®), thaumatin (e.g., Talin®), glycyrrhizic acid salts (MagnaSweet®), or combinations thereof. In one embodiment, the sweetener comprises sucralose. The sweetener may be present in the film in an amount of about 0% to about 5% by weight of the film.

Flavouring Agent

The film may also comprise one or more flavoring agents. Examples include, but are not limited to, vanilla, grape fruit, orange, lime, menthol, liquorice, caramel aroma, honey aroma, peanut, walnut, chocolate, cashew, hazelnut, coconut, coffee, almonds, pineapple, strawberry, raspberry, apple, pear, peach, apricot, blackberry, cherry, pineapple, orange, plum essence, essential oils, essences, extracts, powders, acids such as citric acid or lactic acid, sodium citrate, clove oil, bay oil, anise, thyme, cedar leaf oil, nutmeg, cinnamon, menthol, peppermint, wintergreen, spearmint, eucalyptus, mint, savoury flavourings, or any combination thereof. The flavouring agent may be present in the film in an amount of about 0% to about 5% by weight of the film.

Dosage Forms

As one of skill in the art will appreciate, film-based products in accordance with the invention may be provided in various forms, e.g. as film strips or wafers, multi-layered films, tablets formed from a multi-layered film, capsules, and the like.

Matrix

The present film-based dosage form incorporates a matrix fill. The matrix may be a liquid, flowable gel, or viscous semi-solid. Generally, the properties of the matrix will vary based on the end-product, for example, the matrix may be in a gel or semi-solid form for incorporation in a film strip or wafer, but may be in a liquid or gel form for incorporation into a capsule.

The matrix generally comprises a target molecule, i.e. a molecule of low aqueous solubility, solubilized in a micellar formulation comprising at least a detergent, and optionally comprising one or more of, a lipase, a plasticizing agent and/or an emulsifying agent, in an aqueous solvent. The micelles formed are preferably nanomicelles, e.g. micelles having a diameter in the range of about 5 to 500 nm, preferably 10-200 nm, e.g. 10-100 nm.

The present matrix formulation comprises at least one detergent. The detergent may be an ionic, non-ionic or zwitterionic detergent. Detergents are amphipathic molecules, containing a polar hydrophilic head group attached to a long-chain hydrophobic carbon tail. The polar head group of ionic detergents contain either a positive (cationic) or negative (anionic) charge.

Anionic detergents typically have negatively-charged sulfate or sulfonate groups as the hydrophilic head; whereas cationic detergents contain a positively-charged ammonium group. Bile acids, such as cholic acid, deoxycholic acid, glycocholic acid, chenodeoxycholic acid, taurocholic acid, glycodeoxycholic acid, taurodeoxycholic acid, or a salts thereof, and aliphatic sulphate esters (e.g., sodium dodecyl sulphate or sodium lauryl sulfate) are examples of anionic detergents, and quaternary ammonium salts of acetates, chlorides, or bromides are examples of cationic detergents.

Non-ionic detergents have a neutral, polar head group. Non-ionic detergents are typically based on polyoxyethylene or a glycoside. Polyoxyethylene detergents have a tail composed of hydrophobic oxyethylene or ethylene glycoether chains. Examples of polyoxyethylene-based detergents include ethoxylates, PEGylates and metabolites thereof, including Tweens such as polysorbate 20 (polyoxyethylene (20) sorbitan monolaurate), polysorbate 40 (polyoxyethylene (20) sorbitan monopalmitate), polysorbate 60 (polyoxyethylene (60) sorbitan monostearate), polysorbate 80 (polyoxyethylene (80) sorbitan monooleate), alkylphenol ethoxylates such as nonoxynols and Triton™, and the Brij™ compounds, e.g. Brij 20 (polyoxyethylene (20) cetyl ether) or Brij 35 (polyoxyethylene (23) lauryl ether). A polyethylene glycol glyceride ester may also be used, e.g., Gelucire 33/01, Gelucire 37/02, Gelucire 39/01, Gelucire 43/01, Gelucire 44/14, Gelucire 50/02, Gelucire 50/13, Gelucire 53/10, or Gelucire 62/02. Glycosidic-based detergents have a sugar, such as glucose or maltose, as their uncharged hydrophilic headgroup, and may have an alkyl polymer tail. Examples include octyl thioglucoside and maltosides. Fatty acid esters of sorbitol, such as sorbitan monolaurate, sorbitan monostearate and sorbitan tristearate, fatty acid esters of glycerol, such as glycerol monostearate and glycerol monolaurate and fatty acid esters of sucrose are also non-ionic detergents.

Zwitterionic detergents have a polar head group containing both negatively and positively charged atomic groups, and therefore having an overall neutral charge, e.g. (dimethylmyristylammonio)-propanesulfonate and (tert-Butyl-1-pyridinio)-1-propanesulfonate. Other examples include 3-[(3-cholamidopropyl)dimethylammonio]-1-propane-sulfonate (CHAPS) and 3-[(3-cholamidopropyl)-dimethylammonio]-2-hydroxy-1-propanesulfonate (CHAPSO).

As one of skill in the art will appreciate, the appropriate detergent for inclusion in the present formulation will depend on factors such as the target molecule in the formulation, pH, ionic charges, the desired denaturing effect and the desired end result, including structure and charge of the final product. In an embodiment, the selected detergent is a combination of an ionic detergent such as an aliphatic sulphate ester and a non-ionic detergent such as a polyoxyethylene-based detergent.

The detergent or detergents may optionally be used in conjunction with one or more enzymes that break down lipids (including triglycerides, fats, oils), e.g. a lipase, one or more enzymes that break down proteins, e.g. a protease, and/or one or more enzymes that break down starches. Examples of enzymes that may be used in conjunction with the detergent include, but are not limited to, lipases such as pancreatic lipase (PL), pancreatic lipase-related protein 1 or 2 (PLRP1/PLRP2), hepatic lipase, endothelial lipase, lipoprotein lipase, lysosomal lipase, gastric lipase and lingual lipase. Other examples of suitable enzymes include termamyl (amylase), celluzyme (cellulase), mannanase, pectinase, and proteases such as pepsin, trypsin and chymotrypsin. The enzymes may be naturally occurring enzymes or recombinant enzymes. Individual enzymes or combinations of enzymes may be used.

The amount of detergent in the present formulation is in the range of about 0.01 to 10% by wt of the matrix formulation. The amount of enzyme in the formulation, if used, is in the range of about 0.01 to 10% by wt of the matrix.

The present matrix formulation may optionally include one or more plasticizing agents to attain desired flexibility and mold-releasing properties. Suitable plasticizing agents include, for example, triacetin, monoacetin, diacetin, sorbitol, maltitol, mannitol, xylitol and glycerin. Plasticizing agent may be added to the formulation in an amount ranging from about 0.01 to about 20 wt %, preferably an amount of about 0.1 to about 2 wt % of the formulation.

The present matrix formulation may optionally include an emulsifying agent Examples of suitable emulsifying agents include monoglycerides (e.g. glycerol monostearate), diglycerides, triglycerides (such as, but not limited to, medium-chain fatty acids having 6-12 carbon atoms, e.g. caproic acid, caprylic acid, capric acid and lauric acid), or combinations thereof, esters of mono- and di-glycerides, ethoxylated mono- and di-glycerides, polyvinyl N-pyrrolidone, carboxymethylcellulose, polyoxyethylene, polyoxypropylene, propylene glycol, polyethylene glycol, and copolymers thereof, polyethoxylated oil, lecithin, a phospholipid, mannitol, glycerol, sorbitol, xylitol, maltitol, triethanolamine stearate, acacia, lecithin, bentonite, veegum, and or mixtures thereof. Capmul MCM, Captex 355, Cremophor RH 40, Croscarmellose, Crospovidone, Crospovidone CL, Crospovidone CL-F, Crospovidone CL-M, Imwitor 742, Kollidon CL, Kollidon CL-F, Kollidon CL-M, Labrafac™ Lipophile WL 1349, Labrafil M2125CS, Labrasol, Lutrol F 68, Maisine™ 35-1, Miglyol 812, Pearlitol Flash, Peceol, Plurol Oleique CC 497, Povidone K 17, Povidone K 30, polyethylene glycol 200, polyethylene glycol 400, polyethylene glycol 600, polyethylene glycol 800, polyethylene glycol 1000, polyethylene glycol 2000, polyethylene glycol 3350, Lycasin 80/55 and MCT oil are examples of commercially available emulsifiers. In one embodiment, the emulsifier comprises one or more hydro-alcohols including polyethylene glycol of a molecular weight ranging from about 200 to about 8000 daltons, or a mixture or combination thereof. The present formulation includes emulsifier in amounts ranging from about 0.01 to about 20 wt %, and preferably about 0.01 to about 5 wt % of the formulation.

It is noted that some compounds may have multiple functions, and thus, satisfy multiple roles in the present film, for example, polyoxyethylene-based detergents also exhibit properties of an emulsifier, sorbitol-based compounds function as both a detergent and an emulsifier, lecithin functions as an emulsifier and plasticizer, and glycerol functions as both an emulsifier and a plasticizer. Accordingly, depending on the compounds in the formulation, fewer compounds may be required in order to satisfy the detergent, emulsifier and plasticizer functions.

The present matrix formulation may include a stabilizing agent such as xanthan gum, locust bean gum, guar gum and carrageenan, in amounts ranging from about 0.01 to about 10 wt %, preferably about 0.1 to about 2 wt % of the formulation.

The present matrix formulation may also include one or more saliva stimulating agents such as a food acid, e.g. citric, lactic, malic, succinic, ascorbic, adipic, fumaric or tartaric acid, or mixtures thereof. Preferred food acids are citric, malic and ascorbic acids. The amount of saliva stimulating agent suitable for inclusion in the present formulation may range from about 0.01 to about 12 wt %, preferably about 1 wt % to about 10 wt %.

The present matrix formulation may additionally include a thickening agent such as methylcellulose, carboxyl methylcellulose, and the like, in amounts ranging from about 0.01 to about 20 wt %, and preferably about 0.01 to about 5 wt %.

The present matrix formulation may further include one or more pharmaceutically acceptable adjuvants or carriers. The expression "pharmaceutically acceptable" means acceptable for use in the pharmaceutical arts, i.e. not being unacceptably toxic, or otherwise unsuitable for administration to a mammal. Examples of pharmaceutically acceptable adjuvants include, but are not limited to, diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for oral administration via tablet, capsule, lozenge, solution or suspension in an aqueous or non-aqueous liquid, an oil-in-water or water-in-oil liquid emulsion, an elixir or syrup are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids, magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol, agar; alginic acids; water; isotonic saline and phosphate buffer solutions, wetting agents, lubricants, stabilizers, anti-oxidants and preservatives.

Solvent

The balance of the matrix formulation is an aqueous solvent.

Sweetener

The matrix formulation may also include one or more sweeteners, as exemplified above, in amount of about 0.01% to about 5% by weight of the formulation. The sweetener may be the same or different from the sweetener(s) included in the film base.

Flavouring Agent

The matrix formulation may also include one or more flavouring agents, as exemplified above, in amount of about 0.01% to about 5% by weight of the formulation. The flavouring agent may be the same or different from the flavouring agent(s) included in the film base.

Other Excipients

The film base or matrix may comprise one or more of the following additional excipients: a humectant, inorganic salts, antioxidants, emulsifiers, protease inhibitors or colorants. Non-limiting examples of humectants include propylene glycol or glycerol. Examples of inorganic salts include sodium, potassium, calcium and zinc salts, especially sodium chloride, potassium chloride, calcium chloride, zinc chloride and sodium bicarbonate. Examples of antioxidants include tocopherol, deteroxime mesylate, methyl paraben, ethyl paraben, ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol and mixtures thereof. Examples of protease inhibitors include, but are not limited to, bacitracin and bacitracin derivatives such as bacitracin methylene disalicylates, soybean trypsin and aprotinin. Examples of emulsifiers include lecithins (e.g. E322, E342), polyglycerol polyridnoleate (e.g. PGPR, E476), citric acid esters (e.g. E472c) and ammoniumphosphatide (e.g. E442) and sorbitan tristearate (e.g. STS, E492). Such additional additives may comprise combined between about 1 to about 5 wt % of the shell or matrix. Bacitracin and its derivatives preferably comprise between 1.5 and 2 wt % of the shell or matrix, while soya bean trypsin and aprotinin preferably comprise between about 1 and 2 wt % of the shell or matrix. Examples of colorants include, caramel, red, yellow, black or blends, ferric oxide, etc.

The film base or matrix may include an anti-microbial agent. Antimicrobial agents include: benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol or menthol. In one embodiment, one or more essential oils that confer antimicrobial properties may be included in the film base and/or matrix. Preferably, the amount of a selected essential oil for use is sufficient to provide antimicrobial efficacy while not changing the physical characteristics of the film base or matrix, e.g. an amount ranging from 0.01 to 15 wt % (but may exceed this range). Generally, an oil such as thymol, methyl salicylate and/or eucalyptol may be present in an amount of about 0.01 to about 4 wt %, preferably about 0.50 to about 3.0 wt %, and even more preferably from about 0.70 to about 2.0 wt %. An oil such as menthol may be added in an amount ranging from about 2.0 to about 10 wt %, and even more preferably from about 3 to about 9 wt % of the formulation. The appropriate amount of a selected anti-microbial oil can readily be determined by one of skill in the art.

Saliva stimulating agents may be added to the film base or matrix. Examples of saliva stimulating agents include food acids such as citric, lactic, malic, succinic, ascorbic, adipic, fumaric and tartaric acids. Preferred food acids are citric, malic and ascorbic acids. The amount of saliva stimulating agent suitable for inclusion in the film and/or matrix may range from about 0.01 to about 12 wt %, preferably about 1 wt % to about 10 wt %.

The film base or matrix may also include one or more absorption enhancers, each in an amount of about 1-5% by wt of the film base or matrix. Examples of absorption enhancers include solubilization agents; charge modifying agents; pH control agents; degradative enzyme inhibitors; modulatory agents of epithelial junction physiology, such as nitric oxide (NO) stimulators, chitosan, or chitosan derivatives; vasodilator agents; selective transport-enhancing agents; stabilizing delivery vehicles, carriers, supports or complex-forming species with which exendin(s) is/are effectively combined, associated, contained, encapsulated or bound to stabilize the active agent for enhanced mucosal delivery; small hydrophilic penetration enhancers; emulsifiers, mucolytic or mucus clearing agents (e.g. mucoadhesive and mucosal delivery-enhancing agents); membrane penetration-enhancing agents such as e.g., (i) a surfactant, (ii) a bile salt, (Iii) a phospholipid or fatty acid additive, mixed micelle, liposome, or carrier, (iv) an alcohol, (v) an enamine, (iv) an NO donor compound, (vii) a long-chain amphipathic molecule, (viii) a small hydrophobic penetration enhancer, (ix) sodium or a salicylic acid derivative, (x) a glycerol ester of acetoacetic acid, (xi) a cyclodextrin or beta-cyclodextrin derivative, (xii) a medium-chain fatty acid, (xiii) an amino acid or salt thereof, (xiv) an N-acetylamino acid or salt thereof, (xv) an enzyme degradative to a selected membrane component, (xvi) an inhibitor of fatty acid synthesis, (xvii) an inhibitor of cholesterol synthesis; or (xviii) any combination of the membrane penetration enhancing agents of (i)-(xviii)).

Cooling agents may be added to the film base or matrix to increase its boiling point and thereby prevent bubble formation. An example of a cooling agent that may be added is monomenthyl succinate, in an amount ranging from about 0.001 to about 2.0 wt %, preferably about 0.2 to about 0.4 wt % of the film or matrix. Other suitable cooling agents include menthol carboxamide (WS-3), N,2,3-trimethyl-2-isopropyl butanamide (WS-23), ethyl 3-(p-menthane-3-carboxamido)acetate (WS-5), (1R,2S,5R)—N-(4-methoxyphenyl)-p-menthanecarboxamide (WS-12), N-ethyl-2,2-diisopropylbutanamide (WS-27), N-cyclopropyl-5-methyl-2-isopropylcyclo-hexanecarboxamide, N-(1,1-dimethyl-2-hydroxyethyl)-2,2-diethylbutanamide) (WS-116), menthoxyethanol, and the like.

Additional pharmaceutical excipients useful for the film base or matrix fill as described herein include, for example, the following: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); chelating agents (edetate disodium, ethylenediaminetetraacetic acid and salts, edetic acid); coating agents (sodium carboxymethylcellulose, cellulose acetate, cellulose acetate phthalate, ethylcellulose, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax).

In an embodiment, the matrix comprises a micellar formulation comprising a detergent, a lipase, a plasticizing agent, an emulsifying agent and an aqueous solvent, and a target molecule solubilized in the matrix, and is combined with a film base comprising one or more of gelatin, collagen, acrylates, methacrylates or copolymers thereof, pectin and alginate, a plasticizer and an aqueous solvent.

Target Molecule

The matrix formulation is not particularly restricted with respect to the target molecule that may be incorporated therein for delivery. The present film-based dosage form is, however, particularly useful for the delivery of target molecules that have low solubility in water. Target molecules include pharmaceutical agents, nutraceuticals, and the like.

Examples of target molecules include pharmaceutical agents such as, but not limited to: protein-based pharmaceutical agents such as insulin, heparin, low molecular weight heparin, hirulog, hirugen, huridine, interferons, interleukins, cytokines, mono- and poly-clonal antibodies, immunoglobins, chemotherapeutic agents, vaccines, glycoproteins, bacterial toxoids, hormones, calcitonins, growth factors such as insulin like growth factor (IGF), glucagon like peptides (GLP-1), protein-based drugs, e.g. thrombolytic compounds, erythropoietin and platelet inhibitors; nucleic acid-based pharmaceutical agents such as DNA, RNA, gene therapeutics and antisense oligonucleotides; antimicrobial agents, such as triclosan, cetyl pyridium chloride, domiphen bromide, quaternary ammonium salts, zinc compounds, sanguinarine, fluorides, alexidine, octonidine, and the like; non-steroidal anti-inflammatory drugs, such as aspirin, acetaminophen, ibuprofen, ketoprofen, diflunisal, fenoprofen calcium, naproxen, tolmetin sodium, indomethacin, and the like; anti-tussives, such as benzonatate, caramiphen edisylate, dextromethorphan hydrobromide, chlophedianol hydrochloride, and the like; decongestants, such as pseudoephedrine hydrochloride, phenylepherine, phenylpropanolamine, pseudoephedrine sulfate, and the like; anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, cetirizine, levo cetirizine and the like; expectorants, such as guaifenesin, ipecac, potassium iodide, terpin; anti-diarrheals, such a loperamide, and the like; H2-antagonists, such as famotidine, ranitidine, and the like; proton pump inhibitors, such as omeprazole and lansoprazole; nonselective CNS depressants, such as aliphatic alcohols, barbiturates and the like; nonselective CNS stimulants such as caffeine, nicotine, nicotine polacrilex, nicotine in combination with alkaline agents, strychnine, picrotoxin, pentylenetetrazol and the like; drugs that selectively modify CNS function such as phenyhydantoin, phenobarbital, primidone, carbamazepine, ethosuximide, methsuximide, phensuximide, trimethadione, diazepam, benzodiazeplnes, phenacemide, pheneturide, acetazolamide, suithlame, bromide, and the like; anti-parkinsonism drugs such as levodopa, amantadine and the like; analgesic-antipyretics such as salyicates, phenylbutazone, indomethacin, phenacetin and the like; sychopharmacological drugs such as chlorpromazine, methotrimeprazine, haloperidol, clozapine, reserpine, imipramine, tranylcypromine, phenelzine, MC-4 receptor antagonist, lithium and the like; hypnotics, sedatives, antiepileptics, awakening agents; vitamins and minerals; sildenafil citrate; PPY (3-36); decapeptide; KSL-W (acetate), fluor; anti-diabetic drugs, e.g. metformin, metformin HCL, glyburide and insulin secretart agent, insulin stimulators, fat metabolizers, carbohydrates metabolizers, insulin, cholesterol lowering agents like statins, exenatide, GLP-1, etc.; opioid analgesics such as alfentanil, allylprodine, alphaprodine, anileridine, benzylmorphine, bezitramide, buprenorphine, butorphanol, clonitazene, codeine, cocaine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazine, fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, diamorphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, mixed mu-agonists/antagonists, mu-antagonist combinations, mixtures of any of the foregoing, and the like; and pharmaceutical agents derived from plant material, such as cannabinoids and derivatives thereof, terpenes, Paclitaxel™, plant-derived vitamins, plant-derived proteins (soya, lentils), and the like. As one of skill in the art will appreciate, the present matrix formulation may comprise two or more target molecules that exhibit complementary activity, and which do not interact in any adverse manner.

The term "cannabinoid" and "cannabinoid derivative and analogues" is used herein to refer to a class of diverse chemical compounds that act on cannabinoid receptors, e.g. cannabinoid receptor type 1 (CB1) and cannabinoid receptor type 2 (CB2), in cells that repress neurotransmitter release in the brain. Cannabinoids include the endocannabinoids (produced naturally in the body by humans and animals, such as arachidonoyl-ethanolamide (anandamide), 2-arachidonoyl glycerol (2-AG) and arachidonyl glyceryl ether (noladin ether)); the phytocannabinoids (found in *cannabis* and some other plants such as tetrahydrocannabinol (THC), cannabidiol (CBD) and cannabinol (CBN); synthetic cannabinoids (manufactured artificially), and functionally equivalent derivatives and analogues of any of these. Examples of cannabinoids include, but are not limited to, cannabidiol (CBD), cannabidiol acid (CBDA), cannabinol (CBN), cannabigerol (CBG), cannabicyclol (CBL), cannabivarin, (CBV), cannabigerol acid (CBGA), cannabidivarin (CBDV), cannabidivarin acid (CBDVA), cannabinovarin (CBNV), cannabigerovarin (CBGV), cannabichromene (CBC), cannabichromevarin (CBCV), cannabigerol monomethyl ether (CBGM), naphthoylindoles such as JWH-018, JWH-073, JWH-398, JWH-200, JWH-081, 4-methyl-JWH-073, JWH-015, JWH-122, JWH-220, JWH-019, JWH-007; phenylacetylindoles such as JWH-250 and JWH-203; benzoylindoles such as RCS-4, AM-694 and WIN 48,098; cyclohexylphenoles such as CP 47,497-C8 and CP 47,497; HU-210 and 3-dimethylnepty 11 carboxylic acid homologine 8. Cannibinoids also include tetrahydrocannabinoids and analogs thereof, namely, delta-9 tetrahydrocannabinol (THC or dronabinol) and functionally equivalent compounds, including analogs and derivatives thereof such as delta-8 tetrahydrocannabinol (D8-THC), tetrahydrocannabinol acid (THCA), tetrahydrocannabivarin (THCV), tetrahydrocannabivarin acid (THCVA), nabilone, rimonabant (SR141716), JWH-018, JWH-073, CP-55940, dimethylheptylpyran, HU-210, HU-331, SR144528, WIN 55,212-2, JWH-133, levonantradol, and AM-2201. Mixtures of any of the above cannabinoids is also encompassed. The term "functionally equivalent" as it relates to analogs and derivatives of a cannabinoid refers to compounds which bind a cannabinoid receptor, and/or which exhibit the same or similar therapeutic effect, e.g. at least about 50% of the activity of the cannabinoid from which it is derived.

The matrix comprises the target molecule in an amount of about 0.05% to about 60% by weight of the matrix, preferably 1-50% by wt of the matrix. Generally, the ratio of the weight percentage of target molecule to the combined weight percentage of the matrix is about 1:0.5 to about 1:500.

In one embodiment, a dosage form in accordance with the invention comprises a matrix comprising a cannabinoid, a functionally equivalent derivative thereof or analogue thereof. Such a dosage form is particularly useful in the treatment of pain in a mammal (e.g. human or non-human mammal). Dosages of cannabinoid useful to treat pain are known in the art.

The present matrix formulation may be prepared as follows. The selected target molecule is added to a volume of the selected detergent or mixture of detergents and heated to a temperature in the range of about 35-65° C. The heated combination is mixed to form a clear emulsion in which the target molecule is solubilized by encapsulation in micelles, e.g. generally with high speed mixing. Hot water may additionally be added to the combination to achieve dissolution, e.g. a crystal clear solution. Other non-aqueous components may then be added with heat and stirring. An aqueous solution comprising water-soluble components (e.g. sweetener, flavor, colour) is then added to the emulsion and mixed to form a clear solution. Enzyme, plasticizer, saliva stimulating agent, stabilizing agent and emulsifying agent, if used, may be added once the solution or suspension is made. The mixture is further stirred to form a clear or almost clear solution, and then allowed to cool for storage.

The matrix formulation advantageously provides a formulation in which water insoluble target molecules are solubilized without using alcohols, i.e. an alcohol-free formulation. In addition, the formulation is prepared using hydrogenation methods to form a clear aqueous solution that exhibits improved bioavailability. As used herein, the term "clear" is intended to refer to a solution or aqueous solution that is free, or essentially free, of visible particles of undissolved compound. A clear solution or clear aqueous solution includes, thus, both solutions as well as very fine dispersions that remain clear upon sitting undisturbed for one hour or more. Essentially in a clear solution no visible (to the naked eye) particles or micelles are present.

Method of Film-Based Dosage Form Manufacture

The present film-based dosage form may be prepared using established manufacturing processes.

Figure 2:
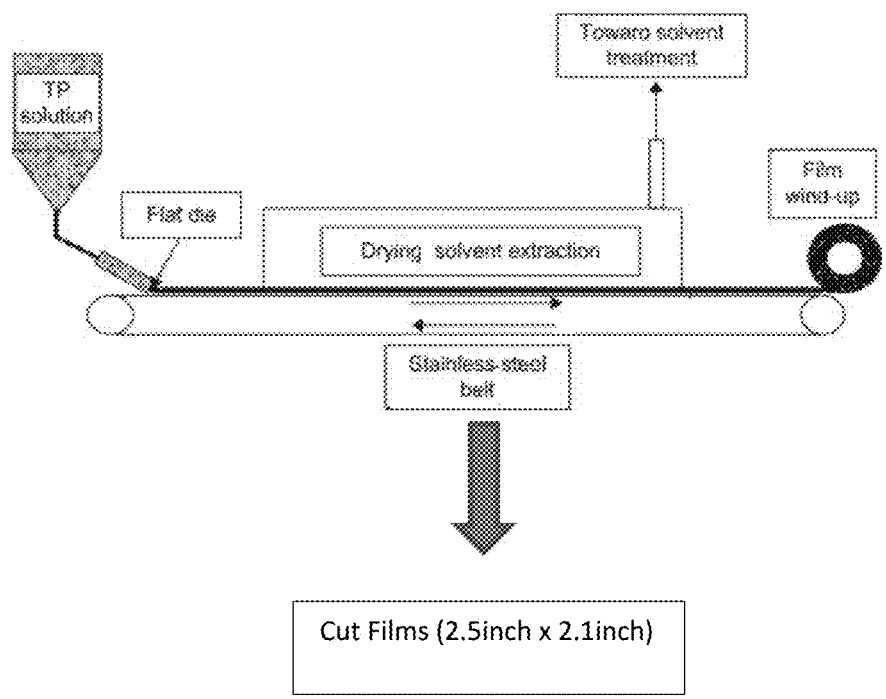
FIG. 2 generally illustrates a slot-extrusion method used to make edible film.

Films, including layered films, may be made using a slot-extrusion method as generally illustrated in FIG. 2. Generally, the film is prepared by blending the dry ingredients (e.g. film-forming agents) together and mixing with liquid ingredients including water, other solvents and/or an aqueous phase including water soluble ingredients, to form a homogeneous liquid blend. The matrix including the solubilized target molecule is combined with the liquid film. The film is then extruded/cast and coated onto a moving belt or drum for drying/cutting/rolling.

Capsules may be formed by a variety of processes which are generally known to those of skill in the art, including the rotary die encapsulation process. In the traditional rotary die process, encapsulation machines form two flexible film sheets or ribbons (soft film ribbons are formed from the capsule components, including at least one film-forming agent, a plasticizer, and a solvent) are synchronously guided over rollers and fed to and between two dies. For example, a left and right ribbon each pass over rollers that feed the ribbons to (and between) two mated die rolls. The die rolls, whose surface architecture determines the size and shape of the resultant capsules, cut the shells from the ribbons as the ribbons roll between the die rolls. A positive displacement pump simultaneously delivers the matrix fill material into a heated wedge that sits between the rotary dies. The pump injects matrix fill, such as a liquid fill material, into the die cavities between ribbons just before the die rolls cut the ribbons and seal the two cut halves of the ribbon together to form a capsule. The capsules are then dried and allowed to harden.

The capsule shell and encapsulated matrix fill generally comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft capsule shell and encapsulated matrix fill comprises an outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the soft capsule shell and encapsulated matrix fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules are known See Remington's *Essentials of Pharmaceutics*, Pharmaceutical Press Publishing Company, London, UK, 1$^{st}$ Edition, 2013.

Advantages

The present invention advantageously provides a means to administer low solubility target molecules to an individual. The film-based dosage form incorporates a matrix comprising a micellar formulation which functions to encapsulate and solubilize the target molecule, thereby increasing bioavailability of the target molecule on administration.

The film base, which is readily soluble on oral administration, provides a dosage form that is easy to administer and which is quickly broken down in the body. The film dissolves by absorbing water when immersed in a wet environment such as the oral cavity. Thus, the film-based dosage form is useful for the oral administration, particularly for those who have difficulty swallowing hard dosage forms such as tablets, e.g. pediatric and geriatric individuals.

In addition, the micellar matrix of the present film-based dosage form is stable in the harsh gastrointestinal environment, and exhibits release of the target molecule in the intestine for absorption into the blood stream to provide a dosage form in which the target molecule is bioavailable.

Further, the present film-based dosage forms are useful for the administration of target molecules that have a strong or undesirable aroma and/or flavour. The target molecules are encapsulated within micelles, and incorporated with a film base that helps to mask any undesirable flavour and/or aroma of its contents, providing, at least, a flavourless and/or aroma-less administrable form, or a dosage form with a desirably flavoured film. Thus, the present film-based dosage form is particularly useful for the administration of cannabinoids and related compounds.

The present film-based dosage forms may also be used to prepare a beverage product comprising target molecules such as cannabinoids. A cannabinoid-containing film or capsule may be added to an aqueous solution to prepare a beverage. The aqueous solution may include additional additives such as nutrients, electrolytes, caffeine, flavours, colours, etc. The film or capsule may also be incorporated within a tea or coffee pod product. The film or capsule protects the target molecule, such as a cannabinoid, within the pod until the pod is exposed to water, and then the film or capsule dissolves to release the cannabinoid.

Embodiments of the present invention are described by reference to the following specific examples which are not to be construed as limiting.

Example 1—Soft Cansules

A film base was prepared from a mixture of gelatin, glycerin, potato starch, lecithin, stevia extract, orange flavor and water, in the proportions indicated below. The components, up to a weight of 200 kg, were placed in a cooking tank with 800 L of capacity and mixed with heating. The amounts, by % weight, were as follows:

| Film Component | % wt |
|---|---|
| Gelatin 170-180 Bloom Pigskin | 33.58 |
| Glycerin 99.5% | 28.79 |
| Potato Starch | 11.5 |
| Lecithin | 0.96 |
| *Stevia* extract | 0.0144 |
| Orange Flavor | 0.191 |
| Purified Water | 24.96 |

The cooking tank was heated to 80-90° C., and the temperature was maintained for a period of 1-3 hours. The temperature of the cooking tank was then reduced to 55° C. until air bubbles were completely removed in the film.

The matrix filling comprised the following ingredients:

| Matrix Component | % wt |
|---|---|
| CBD/THC oil or hemp oil | 0.5% |
| Na lauryl sulfate (SLS) (ionic detergent) | 3% |
| Brij 80 detergent (Tween) | 2% |
| vitamin E (d,1-α-tocopheryl acetate) (emulsifier) | 5% |
| omega-3 fatty acid ethyl ester (Incromega ™ 3322) (emulsifier) | 1.5% |
| mono-, di-glycerides of caprylic acid (detergent) | 15% |
| polyoxyl 35 (Cremophor ™ EL) (emulsifier) | 20% |
| glycerin (plasticizing agent) | 25% |
| triethanolamine stearate (emulsifier) | 5% |
| pancreatic lipase related protein 2 and 1 (lingual lipase) | 3% |
| sodium citrate (saliva stimulating agent) | 0.1% |
| distilled water | 27% |

The method of making the matrix formulation was as follows. A water soluble formulation comprising cannabidiol and THC was prepared by admixing the cannabidiol oil with the detergents, Na lauryl sulfate+Brij 80 (polyoxyl ether 80). The cannabidiol oil contained 80 wt % cannabidiol (CBD) and 20% oil. The mixture was heated with stirring to a temperature of about 60° C. and mixed at 1000-1500 rpm until a clear viscous emulsion phase with dissolved CBD oil was formed (cannabidiol emulsion). Water was boiled at 212° F. The heated water was then slowly added to the cannabidiol emulsion until a crystal clear solution was formed. In a separate container, Vitamin E oil, Omega-3 oil fatty acid ethyl ester, mono/di-glyceride of caprylic acid detergent, Cremophor and glycerin were combined and mixed to form an emulsion. This emulsion was then added to the oil-water mixture at 60° C. slowly while stirring continuously at 1000 rpm. An aqueous solution comprising water-soluble components, if any (e.g. sweetener, flavor, colour), would be added to the emulsion at this stage and mixed to form a clear solution. Enzyme, saliva stimulating agent and emulsifying agent (triethanolamine stearate) were then added to the solution.

The mixture thus prepared was stirred additionally for 30-45 minutes to form an essentially clear nanomicellar solution comprising solubilized CBD. The solution was then cooled down slowly to room temperature and stored in a brown glass bottle.

Chewable soft capsules of 20-oval size were produced using conventional soft capsule rotary die machinery and were filled with the matrix filling as shown in FIG. 1. Two plasticized gelatin ribbons (prepared from the shell film in the rotary-die machine) are continuously and simultaneously fed with matrix fill between the rollers of the rotary die mechanism. The forced injection of the matrix fill between the two ribbons causes the gelatin to swell into the left- and right-hand die pockets which governs the size and shape of the softgels as they converge. As the die rolls rotate, the convergence of the matching dies pockets hermetically seals and cuts out the filled capsules.

Capsules were dried in a tumble drier where cold air was initially used to congeal the capsule mass and keep the shell shape integrated. Drying was then completed using a tunnel dryer. Dried capsules had a 9.8% water content, and firm texture (a hardness peak of 91.9 gram force) as measured using a TA-XT2 texture analyzer (Texture Technologies, Scarsdale, N.Y.) using a standard two bite texture profile analysis with a 0.25 inch diameter probe at room temperature.

A chewable soft capsule matrix containing solubilized THC/CBD resulted.

Example 2—A Chewable Softgel Formulation

A chewable softgel formulation was prepared including:

| % wt | Component |
|---|---|
| about 2.3 to about 2.4 wt % | citric acid; |
| about 46.4 to about 48.4 wt % | gelatin or hydrogenated starch hydrolysate |
| about 18.4 to about 19.2 wt % | glycerin; |
| about 14.7 to about 15.3 wt % | xylitol; |
| about 9.3 to about 9.7 wt % | calcium ascorbate; |
| about 6.1 to about 6.3 wt % | water; |
| about 0.30 to about 0.32 wt % | zinc ascorbate; |
| about 0.53 to about 0.56 wt % | flavoring; and |
| about 0.0989 to about 0.101 wt % | an apple extract. |
| About 0.1 to 0.3 wt % | THC or CBD oil; and |
| About 0.5% | SDS in water |

The selected cannabinoid was mixed with SDS and water to form micelles incorporating solubilized cannabinoid.

To form the gelatin film, the remaining components were mixed together with heat to form a chewable film. The cannabinoid-containing micelles were added to the film.

The resulting chewable film comprised solubilized cannabinoid that is readily bioavailable on administration. The apple extract in the film is loaded with polyphenols to aid in the elimination or prevention of bad breath, dental caries and gingivitis on administration.

Example 3—EasyBurst Capsules Formulation

A film base was prepared as described in Example 1.
A matrix formulation was prepared, also as described in Example 1, comprising the following components:

| Component | % by wt |
| --- | --- |
| CBD | 5.000 |
| Avicel | 0.250 |
| Thymol NF | 0.400 |
| Menthol NF | 0.550 |
| Methyl Salicylate | 0.500 |
| Mint flavor | 8.500 |
| Citric Acid | 0.750 (saliva stimulating agent) |
| Copper gluconate | 1.250 |
| Purified water, USP | 68.500 |
| Sodium lauryl sulfate | 1.500 (surfactant, detergent) |
| Aspartame | 6.500 (sweetener) |
| Cooling agent | 0.075 |
| Glycerin | 5.000 (plasticizer) |
| Polysorbate 80 NF | 0.550 (emulsifier) |
| Atmos 300 | 0.550 (emulsifier) |
| FD&C Green #3 | 0.009 |
| Macrogolglycerol | 13.116 |
| D&C Yellow #10 | 0.002 |
| Trypsin and Chymotrypsin | 0.005 |

The matrix filling was prepared by mixing the ingredients with heat to 70° C., and stirring with a high speed stirrer continuously until a homogeneous clear mixture was obtained in which the CBD was solubilized.

Chewable soft capsules were produced using conventional soft capsule machinery and were filled with the matrix filling using the following parameters:
Encapsulation Parameters (Quality Parameters):

| Matrix Formulation | |
| --- | --- |
| Gel Age (hrs) | 4-72 |
| Machine Die Speed (rpm) | 3.0 |
| Die pressure (psi) | 75 |
| Target Ribbon Thickness | 0.028 inches (Range 0.025-0.03 inches) |
| Fill weight (mg) | Target: 960 mg |
| Alert Limits: | 941-979 mg |
| Control limits: | 912-1008 mg |

Example 4—Clinical Study in Humans

A clinical trial has been conducted to assess the pharmacokinetic (PK) properties of the film-based capsule dosage form of Example 1 containing either 10 mg or 20 mg doses, in 17 healthy volunteers. Blood samples were taken at prior to administration, and then at 15, 30 45, 60, 90, 120, 180, 240, 300, 360 and 420 minutes following administration of the dosage forms.

Representative results of this trial are shown in Table 1 below, comparing pharmacokinetics and bioavailability of 10 mg and the 20 mg dosage forms to the drug, Sativex, containing 10 mg of CBD.

TABLE 1

| CBD Dose (mg) | Cmax (ng/ml) | Tmax (h) | AUC (ng/ml*h) |
| --- | --- | --- | --- |
| 10 mg | 2.97 [2.97-3.01] | 2.97 [2.35; 3.75] | 8.89 [7.49; 10.55] |
| 20 mg | 23.42 [23.97-27.79] | 2.45 [2.73; 4.36] | 144.77 [121.76; 172.14] |
| Sativex 10 mg | 1.80 [1.51-2.15] | 2.92 [2.31; 3.69] | 6.65 [5.59; 7.91] |

The results of the study show that significantly higher CBD plasma levels (Cmax) were achieved using the CBD capsules of Example 1 as compared to the CBC plasma levels achieved with Sativex. Thus, the present CBD capsules demonstrated superior pharmacokinetic values and bioavailability. The bioavailability of CBD using the present 10 mg CBD capsules was shown to be 134% greater than the bioavailability of CBD achieved by Sativex.

Further, this study demonstrated a significant dose response comparing 10 mg and 20 mg, which can translate to personalized clinical effect optimization, and confirms efficacy of the present dosage form comprising CBD to treat pain in a subject (e.g. a mammal, including a human or non-human mammal).

Example 5—Gastrointestinal Stability

The main obstacle for oral drug delivery is the harsh environment of the gastrointestinal tract. The dissociation of the nanomicelles in the stomach and/or in the intestine causes the release of the encapsulated drug. On the other hand, particle size plays a key role in gastrointestinal absorption, and it is reported that an average diameter less than 300 nm is advantageous for intestinal permeation.

To simulate gastrointestinal conditions, the nanomicellar matrix of Example 1 was incubated at 37° C. for 30 min in commercially available simulated gastric fluid (GF) followed by incubation in simulated intestinal fluid (IF). As shown in Table 2, the average diameter of micelles following both incubations was constant indicating that neither low pH value nor digestive enzymes adversely affect the stability of the nanomicelles (Mean±SD, n=3).

TABLE 2

Stability of Nanomicelles in simulated GF and IF

| | Average Diameter (nm) | Polydispersity index (PdI) |
| --- | --- | --- |
| GF | 58.7 ± 1.1 | 0.12 ± 0.01 |
| IF | 55.4 ± 2.2 | 0.20 ± 0.02 |

No micelle precipitation was found, confirming the stability of both the formulations. Based on these results, it is evident that the micelles may be absorbed at the gastrointestinal level without degradation.

Example 6—Stability in Blood Conditions

After assessing the physical stability of the nanomicellar matrix in gastrointestinal conditions, the matrix of Example 1 was incubated in phosphate buffer saline (PBS, pH 7.4) with and without human serum albumin (HSA, 45 g/L) at 37° C. for 72 h to simulate the blood circulation. The results shown that both matrix formulations were unchanged in PBS and in PBS with HSA over a period of 72 h. The slight increase of the PdI after incubation in PBS with HSA might be due to the coexistence of albumin and nanomicelles. The maximal increase of the sizes was about 10-15 nm, therefore, the nanomicelles are able to maintain their structure in physiological pH conditions and also in the presence of plasma proteins.

TABLE 3

Stability of Nanomicelles in PBS with and without HSA (Mean ± SD, n = 3).

| | Average Diameter (nm) | PdI |
| --- | --- | --- |
| PBS 24 h | 68.0 ± 1.1 | 0.08 ± 0.01 |
| PBS 48 h | 64.1 ± 1.8 | 0.12 ± 0.02 |
| PBS 72 h | 66.6 ± 1.2 | 0.09 ± 0.01 |
| BS + HSA 24 h | 69.6 ± 1.3 | 0.21 ± 0.02 |
| BS + HSA 48 h | 70.6 ± 0.4 | 0.24 ± 0.01 |
| BS + HSA 72 h | 70.9 ± 0.2 | 0.25 ± 0.01 |

PBS: phosphate buffer saline; HSA: human serum albumin; PdI: polydispersity index.

Example 7—In Vitro Release in Gastro Intestinal Fluid

Further studies of CBD dissolution rates from 10 mg and 20 mg CBD capsules of Example 1 in buffers mimicking intestinal and gastric fluids demonstrated surprisingly high dissolution of CBD in the intestinal fluid as follows:

% Release of CBD (10 mg Dose)

| Time (mins) | % Release |
| --- | --- |
| 0 | 0 |
| 10 | 53.1 |
| 20 | 70.4 |
| 30 | 98.6 |

% Release of CBD (20 mg Dose)

| | |
| --- | --- |
| 0 | 0 |
| 10 | 57.1 |
| 20 | 75.3 |
| 30 | 95.6 |

Example 8—Stability Testing Studies

Further stability studies show that the micellar matrix fill of Example 1 is stable at room temperature and higher temperatures (40° C.) for at least 7 months (M). An assay to determine CBD content of the matrix over time was conducted with the following results:

i) At 40° C./75% RH:

| | | 1M | 2M | 3M | 4M | 7M |
| --- | --- | --- | --- | --- | --- | --- |
| CBD 10 mg | Assay (% recovery) | 99.32 | 97.80 | 99.82 | 100.50 | 100.78 |
| | | 99.08 | 96.90 | 99.10 | 99.80 | 99.94 |
| | | 99.41 | 96.30 | 99.87 | 97.40 | 98.7 | ii) At 25° C./60% RH:

| | | 1M | 2M | 3M | 4M | 7M |
| --- | --- | --- | --- | --- | --- | --- |
| CBD 10 mg | Assay (% recovery) | 97.32 | 98.70 | 99.02 | 98.50 | 97.78 |
| | | 98.08 | 97.30 | 97.10 | 98.70 | 96.94 |
| | | 99.11 | 98.10 | 97.07 | 97.20 | 97.03 |

An analysis to determine uniformity of the matrix was also conducted using standard HPLC methods equipped with a variable wave length UV detector and using water:alcohol:acetonitrile (1:0.5:1.5) eluent mixture. The data indicates that the micelle matrix content was uniform. Uniformity of Dosage Unit (% of Label Claim) Products 10 mg Dose

| | | | |
| --- | --- | --- | --- |
| 95.1 | 94.3 | 98.0 | 114.3 |
| 93.9 | 94.5 | 109.8 | 98.5 |
| 94.4 | 93.7 | 98.2 | 97.7 |

20 mg Dose

| | | | |
| --- | --- | --- | --- |
| 93.8 | 94.4 | 98.0 | 99.2 |
| 94.3 | 94.7 | 98.3 | 98.2 |

The invention claimed is:
1. A film-based dosage form comprising:
  i) a film base comprising a film-forming agent, a plasticizer and a solvent; and
  ii) a matrix within the film base comprising a target molecule that exhibits low aqueous solubility, wherein said target molecule is encapsulated in a micellar formulation comprising a detergent and an enzyme in an aqueous solvent.
2. The dosage form of claim 1, wherein the target molecule is a cannabinoid or a derivative or analogue thereof.
3. The dosage form of claim 1, wherein the target molecule is a cannabinoid selected from an endocannabinoid, a phytocannabinoid, a synthetic cannabinoid, a functionally equivalent derivative or analogue thereof or a mixture thereof.
4. The dosage form of claim 1, wherein the target molecule is selected from the group consisting of: cannabidiol (CBD), cannabidiol acid (CBDA), cannabinol (CBN), cannabigerol (CBG), cannabicyclol (CBL), cannabivarin, (CBV), cannabigerol acid (CBGA), cannabidivarin (CBDV), cannabidivarin acid (CBDVA), cannabinovarin (CBNV), cannabigerovarin (CBGV), cannabichromene (CBC), cannabichromevarin (CBCV), cannabigerol monomethyl ether (CBGM), a naphthoylindole, a phenylacetylindole, a benzoylindole, a cyclohexylphenole, 3-dimethylnepty 11 carboxylic acid homologine 8, delta-9 tetrahydrocannabinol (THC), delta-8 tetrahydrocannabinol (D8-THC), tetrahydrocannabinol acid (THCA), tetrahydrocannabivarin (THCV), tetrahydrocannabivarin acid (THCVA), nabilone, rimonabant (SR141716), JWH-018,

JWH-073, CP-55940, dimethylheptylpyran, HU-210, HU-331, SR144528, WIN 55,212-2, JWH-133, levonantradol, AM-2201 and mixtures thereof.

5. The dosage form of claim 1, wherein the detergent is selected from an ionic detergent, non-ionic detergent, zwitterionic detergent or mixtures thereof.

6. The dosage form of claim 1, wherein the detergent comprises an aliphatic sulphate ester and a polyoxyethylene-based detergent.

7. The dosage form of claim 1, wherein the enzyme is selected from the group consisting of pancreatic lipase (PL), pancreatic lipase-related protein 1 (PLRP1), pancreatic lipase-related protein 2 (/PLRP2), hepatic lipase, endothelial lipase, lipoprotein lipase, lysosomal lipase, gastric lipase, lingual lipase, lipolase or a mixture thereof.

8. The dosage form of claim 1, wherein the matrix additionally comprises a plasticizing agent.

9. The dosage form of claim 8, wherein the plasticizing agent is selected from triacetin, monoacetin, diacetin, glycerin, sorbitol, maltitol, mannitol, xylitol and mixtures thereof.

10. The dosage form of claim 1, wherein the matrix additionally comprises an emulsifying agent.

11. The dosage form of claim 10, wherein the emulsifying agent is selected from triethanolamine stearate, a monoglyceride, a diglyceride, esters of mono- or di-glycerides, ethoxylated mono- or di-glycerides, a quaternary ammonium compound, acacia, gelatin, lecithin, bentonite, veegum, and mixtures thereof.

12. The dosage form of claim 1, wherein the matrix comprises sodium lauryl sulfate and a polyoxyethylene detergent, glycerin and a lipase.

13. The dosage form of claim 1, wherein the film-forming agent is selected from gelatin, pullulan, alginic acid or alginate, collagen, methyl cellulose, ethyl cellulose, sodium carboxymethyl cellulose, hydroxypropylmethyl cellulose, hydroxyethyl cellulose, hydroxypropyl cellulose, carboxymethyl cellulose, polyvinyl pyrrolidone, methacrylic acid polymers, methacrylic acid copolymers, acrylic acid polymers, acrylic acid copolymers, polyacrylic acid, acrylate or methylmethacrylate copolymers, polyacrylamides, polyalkylene oxides, carrageanan, polyvinyl alcohol, sodium alginate, polyethylene glycol, glycolide, polylactide, carboxyvinyl polymer, amylose, high amylose starch, hydroxypropylated high amylose starch, pea starch, dextrin, pectin, chitin, chitosan, levan, elsinan and mixtures thereof.

14. The dosage form of claim 1, comprising a secondary film forming agent selected from xanthan gum, tragacanth gum, guar gum, locust bean gum, acacia gum, arabic gum, zein, gluten, soy protein isolate, whey protein isolate, casein and mixtures thereof.

15. The dosage form of claim 1, wherein the film-forming agent comprises one or more of gelatin, collagen, an acrylate, a methacrylate or copolymers thereof, pectin and/or alginate.

16. The dosage form of claim 1, wherein the film-forming agent is selected from acid bone gelatin, pig skin gelatin, chicken skin gelatin, fish gelatin, acid hide gelatin, gelatin hydrolysate, lime bone gelatin and combinations thereof having a Bloom value of 100-250.

17. The dosage form of claim 1, wherein film-forming agent is combined with a non-gelling gelatin hydrolysate.

18. A film-based capsule dosage form comprising:
  i) a film base in the form of a capsule shell comprising a film-forming agent, a plasticizer and a solvent; and
  ii) a matrix contained within the capsule shell comprising a target molecule that exhibits low aqueous solubility in an amount of 1%-50% by weight of the matrix encapsulated in a micellar formulation comprising a detergent in an amount of 0.01% to 10% by weight of the matrix, a lipase in an amount of 0.01 to 10 wt % of the matrix, a plasticizing agent in an amount of 0.01% to about 20% by weight of the matrix, an emulsifying agent in an amount of 0.01% to about 20% by weight of the matrix and an aqueous solvent as the balance of the formulation, wherein the target molecule is solubilized in the matrix.

19. The film-based dosage form of claim 18, wherein the film-forming agent is gelatin, the plasticizer is glycerin, the detergent is sodium dodecyl sulfate and a polyoxyethylene detergent and the target molecule is a cannabinoid.

20. A method of treating pain in a subject comprising administering to the subject a dosage form as defined in claim 2.

* * * * *